United States Patent
Abraham-Fuchs et al.

[11] Patent Number: 5,918,110
[45] Date of Patent: Jun. 29, 1999

[54] METHOD FOR MANUFACTURING A COMBINATION OF A PRESSURE SENSOR AND AN ELECTROCHEMICAL SENSOR

[75] Inventors: Klaus Abraham-Fuchs, Erlangen; Walter Gumbrecht, Herzogenaurach; Christofer Hierold; Thomas Scheiter, both of Munich, all of Germany

[73] Assignee: Siemens Aktiengesellschaft, Munich, Germany

[21] Appl. No.: 08/866,414

[22] Filed: May 30, 1997

[30] Foreign Application Priority Data

May 31, 1996 [DE] Germany ............................ 196 21 996

[51] Int. Cl.$^6$ ................................................... H01L 29/84
[52] U.S. Cl. ................................. 438/48; 438/49; 438/50; 438/53; 438/59
[58] Field of Search ................................. 438/48, 49, 50, 438/53, 59; 129/303, 675 R, 419 PG, 630, 631, 632, 633; 433/6; 257/350, 352

[56] References Cited

U.S. PATENT DOCUMENTS

| | | |
|---|---|---|
| 4,629,424 | 12/1986 | Lauks et al. . |
| 4,716,887 | 1/1988 | Koning et al. . |
| 4,739,380 | 4/1988 | Lauks et al. . |
| 4,771,772 | 9/1988 | DeWitt . |
| 4,874,500 | 10/1989 | Madou et al. . |
| 5,225,063 | 7/1993 | Gumbrecht et al. . |
| 5,343,064 | 8/1994 | Spangler et al. . |
| 5,376,255 | 12/1994 | Gumbrecht et al. . |
| 5,385,659 | 1/1995 | Gumbrecht et al. . |
| 5,554,273 | 9/1996 | Demmin et al. . |
| 5,631,428 | 5/1997 | Catanescu et al. . |
| 5,833,603 | 11/1998 | Kovacs et al. . |

FOREIGN PATENT DOCUMENTS 0 299 778  1/1989  European Pat. Off. .

OTHER PUBLICATIONS

"Integrated pO$_2$, pCO$_2$, pH Sensor System for Online Blood Monitoring," Gumbrecht et al., Sensors and Actuators B, 18–19 (1994) pp. 704–708. No Month.

"Online Blood electrolyte Monitoring with a ChemFET Microcell System," Gumbrecht et al., Sensors and Actuators B1 (1990) pp. 477–480 No Month.

*Primary Examiner*—Charles Bowers
*Assistant Examiner*—Martin Sulsky
*Attorney, Agent, or Firm*—Hill & Simpson

[57] ABSTRACT

In a method for manufacturing a combination of a pressure sensor and an electrochemical sensor, a basic structure for an ISFET is manufactured on a substrate made of silicon. After depositing a nitride layer as a pH-sensitive layer, the region of the ISFET is covered with a protective layer. In a region provided for a pressure sensor, a structured layer of polysilicon, provided as a membrane, is manufactured above a hollow space. Additional method steps for manufacturing electrical terminals of the sensors and, if required, additional integrated components, and for manufacturing printed conductor planes, are carried out in the context of a CMOS process. IMOX layers in the region of the gas sensor are wet-chemically removed down to the nitride layer. A platinum contact and an additional protective layer made of a PECVD oxide and a PECVD nitride are deposited. Additional layer structures for the gas sensor are manufactured. The pressure sensor is etched free either before the gas sensor is etched free, or after the deposition of the additional protective layer.

22 Claims, 5 Drawing Sheets

METHOD FOR MANUFACTURING A COMBINATION OF A PRESSURE SENSOR AND AN ELECTROCHEMICAL SENSOR

BACKGROUND OF THE INVENTION

1. Field of the Invention

The present invention is directed to a method for manufacturing a combination of a pressure sensor and an electrochemical sensor 2. Description of the Prior Art For applications in e.g. medical technology, sensors are used with which a physical quantity can be measured and at the same time chemical determinations (e.g. $pO_2$ value, $pCO_2$ value, pH value, electrolyte concentrations) can be carried out. The electrochemical sensor is e.g. an ISFET (ion-selective field effect transistor). Such sensors are described, for example, in European Application 0 465 708 corresponding to U.S. Pat. No. 5,225,063, U.S. Pat. No. 5,376,255 and in the articles of W. Gumbrecht et al., Sensors and Actuators B. 18–19, 704 to 708 (1994), and Sensors and Actuators B1, 477 to 480 (1990). In German OS 44 41 908, the manufacture of thin film pressure sensors on silicon is described, which can ensue in the context of a standard CMOS process technology. Sensors of this sort, manufactured in surface micromechanics, can be monolithically integrated with further components and can be mounted in a housing at low expense. A combination of a sensor of this sort with other components, in particular with electrochemical sensors, is possible by means of modular integration, i.e., the integration of different components on different chips by mounting the components on a common substrate or in a common housing.

SUMMARY OF THE INVENTION

An object of the present invention is to provide a simple method that can be carried out economically for manufacturing an integrated combination of a physical and an electrochemical sensor.

The above object is achieved in accordance with the principles of the present invention in a method for integrating a micromechanical pressure sensor and an electrochemical sensor on a substrate, wherein electrically conductive region are formed in the substrate and the basic structure of the electrochemical sensor is manufactured on the substrate, this basic structure including at least one electrically insulating layer. The basic structure of the electrochemical sensor is then covered with a protective layer, but a region for the pressure sensor is left free. A sensor layer for the pressure sensor is deposited in the free region, and is structured and is provided with etching openings. A hollow space is etched out between the sensor layer and the substrate. The entire surface of the arrangement produced to this point is covered with a planarization layer of dielectric material. Electrically conductive connections are then made to regions which are provided for electrical connection. A region of the arrangement produced thus far is then etched free, and at least one noble metal electrode for the electrochemical sensor is deposited and structured in this region. An additional protective layer is deposited over the noble metal electrode. Additional layers as required for the particular manner of operation of the electrochemical sensor are then deposited and structured. The sensor layer for the pressure sensor must be exposed to the exterior, and this can be accomplished either between the step for producing the electrically conductive connections and the step for etching free the region for the noble metal electrode, or between this etching step and the step of depositing the additional protective layer for the noble metal electrode.

The inventive method enables, in a simple way, the monolithic integration of a pressure sensor with an electrochemical sensor, which, e.g. as a potentiometric sensor, as an amperometric sensor or as a conductometric sensor, measures electrical voltages, currents or conductivities in liquids that are characteristic for the concentration of a chemical component in the respective liquid. A preferred embodiment of a potentiometric sensor includes an ISFET. Additional components, e.g. transistors of an electronic control and evaluation circuit, can likewise be manufactured in monolithically integrated fashion in the context of the inventive method. This manufacturing process includes method steps known from the manufacture of individual components, such as e.g. the use of masking technology and vaporization processes, dry etching processes, wet etching processes and various photolithography steps. In this method, on a substrate made of semiconductor material, in which further electronic components for an electronic measurement or control circuit are also integrated as needed, a region provided for the electrochemical sensor is prepared to the extent that the part of the sensor involving the substrate is manufactured. In the manufacture of a potentiometric sensor, the basic structure of a conventional ISFET with source and drain regions is, for example, manufactured, including an oxide layer provided for definition of the characteristics of the channel region (threshold voltage) and of the, e.g., pH-sensitive layer (e.g., a nitride layer) covering the structure. In the case of the manufacture of an amperometric sensor, the material of the substrate is covered with an electrically insulating layer, e.g., of $SiO_2$, or preferably also a layer of $Si_3N_4$. Subsequently, this prepared part of the electrochemical sensor, specifically the nitride layer of an ISFET, is covered with a protective layer. The basic structure of the pressure sensor, including a hollow space under a layer provided as a membrane, is manufactured and is covered with a planarizing layer. For the electrical interconnection, fillings of contact holes in the dielectric (intermediate oxide) are manufactured, with multiple layers if necessary, and metallizations are deposited thereupon and are structured as printed conductor planes (simultaneously also for the provided integrated electronic circuits). Further components of the electrochemical sensor are manufactured, for which purpose the nitride layer of the ISFET, or the insulating layer of another type of electrochemical sensor, is partially etched free. The manufacture of one or (dependent on the sensor type) more electrodes for electrical connection is included in these method steps. An oxide layer, and over this a nitride layer, are deposited and structured over the whole surface. The physical sensor is preferably exposed at its exterior by means of dry etching before the wet-chemical etching free of the electrochemical sensor, or after depositing the oxide layer and of the nitride layer. Additional method steps for the manufacture of the electrochemical sensor follow. In this way, it is achieved that the pressure sensor and the electrochemical sensor both have optimal functional characteristics (sensitivity, measurement range, etc.). The entire manufacturing process is compatible with the standard CMOS process (including the standard bi-CMOS process), as described in the textbook VLSI literature. With this method, it is thus possible also to monolithically integrate electronic circuits for controlling the sensors and for evaluating the measurement results. In the method, the manufacture of the optimized micromechanical sensor is enabled by means of a protective layer on the basic structure of the electrochemical sensor, without damaging this basic structure of the electrochemical sensor. The optimized construction of the electrochemical sensor is manufactured in the preceding method steps and in the subsequent ones, without damage to the physical sensor protected by the deposited layer structure.

DESCRIPTION OF THE DRAWINGS

Cross-hatchings have been omitted in the drawings for clarity, as were the parts of the depicted components lying behind the plane of the drawing.

DESCRIPTION OF THE PREFERRED EMBODIMENTS

Figure 1:
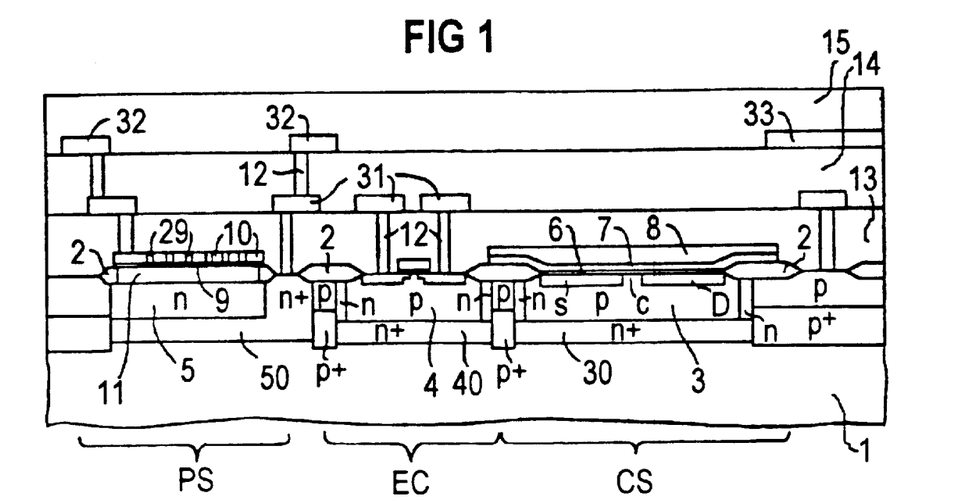
FIGS. 1 and 2 respectively show a cross-section of the structure of intermediate stages of a monolithic integration of a potentiometric sensor with ISFET and of a pressure sensor according to various method steps.

FIG. 1 shows a substrate 1 (e.g. silicon) and various doped regions formed therein. An e.g. highly n-conductive doped region 30, and a p-conductive doped region 3 embedded therein, are formed for the ISFET of a potentiometric sensor CS provided in this exemplary embodiment. An n-conductive or (here as an example) p-conductive doped region 4 inside an oppositely doped region 40 is provided as a trough for the manufacture of a MOSFET as a component of an electronic circuit EC. The e.g. n-conductive doped region 5 is provided as a substrate electrode for the pressure sensor. This region 5 is embedded in a region 50 that is highly doped for the same conductivity type (here, n-conductive), on which a contact (vertical electrically conductive connection 12) is also deposited. The doped regions 30, 40 and 50, provided for the various components, are separated from one another by regions of opposite conductivity. The respective bottommost highly doped portions of these regions can be omitted. The substrate 1 is e.g. silicon, oxidized on the surface region by region, e.g. by means of LOCOS, to form insulating regions 2. These regions 2 form insulation surrounding the individual integrated components, and preferably also serve as a sacrificial layer, to be removed later, in the area of the pressure sensor. In the p-doped region 3, the source S and the drain D of the ISFET are manufactured by means of an n-doping. A further implantation can be provided in the channel region in order to set the electrical characteristics thereof, in particular the threshold voltage. A typical separate thermal oxidation, of the type typical for ISFETs, for the adaptation of the electrical characteristics of the channel region C ensues before the method steps for generating the physical sensor. Instead of this thermal oxidation, a deposition of an oxide for manufacturing an oxide layer 6 on the channel region C, as well as a subsequent depositing of a pH-sensitive layer 7 (preferably a nitride layer) can ensue before the method steps provided for the physical sensor. Due to the demands placed on the quality of this pH-sensitive layer 7, the manufacture of this layer preferably ensues with a nitride layer that is 10 nm to 100 nm thick being deposited in the region of the ISFET to be manufactured, using LPCVD (low-pressure chemical vapor deposition).

This nitride layer is subsequently covered with a protective layer. For this protective layer, e.g. an additional oxide layer 8 can first be deposited. This oxide layer is e.g. a TEOS (tetraethylorthosilicate) layer with a thickness of 100 nm. The nitride layer 7 and this oxide layer 8 are removed in the areas outside the ISFET in the same method step by means of phototechnology, as shown in FIG. 1. A TEOS layer 9, e.g. about 30 nm thick, provided for the physical sensor, is then deposited. If this TEOS layer 9 suffices as a protective layer for the nitride layer of the ISFET, the previously mentioned additional oxide layer 8 can be omitted. A layer, e.g. about 400 nm thick, of amorphous silicon or polysilicon is then deposited on this TEOS layer 9 as a sensor layer 10, which in this example is n-doped and is provided for the membrane of the pressure sensor. Corresponding to the desired dimensions of the pressure sensor, these two layers 9, 10 are etched to form the structured layer depicted in FIG. 1, which is present only in the region of the pressure sensor PS, and is deposited there on an auxiliary layer that can be etched selectively to the silicon, which auxiliary layer serves as a sacrificial layer. It is simplest to use a flat insulating region 2, manufactured by means of thermal oxidation of the substrate surface, as this auxiliary layer. In the region of the electrochemical sensor CS, the TEOS layer 9, which by comparison is very thin and is not separately designated in FIG. 1, can be maintained for the time being.

In an embodiment, there next ensues a first deposition and structuring of polysilicon ("poly 1") for the gate electrodes of the MOSFETs of the circuit. For the manufacture of the membrane of the pressure sensor, after deposition of the oxide layer 8, there ensues a second deposition and structuring of polysilicon ("poly 2"). Instead of this, the protective layer can be deposited before the deposition of the gate electrodes, but it is also removed in the region of the circuit EC, so that the gate electrodes can also be deposited and structured together with the membrane of the pressure sensor, in the same method step.

After the structuring, the layer 9, 10 of the pressure sensor PS is exposed toward the substrate to the extent required. For this purpose, etching openings 29 are manufactured in the sensor layer 10, which are subsequently used to etch out a hollow space 11 between the substrate 1 and the sensor layer 10. The sensor layer 10 is exposed toward the substrate through this hollow space to the extent required for the intended size and degree of movement of the membrane. The etching openings 29 are subsequently sealed, so that the hollow space 11 is outwardly sealed. This can take place e.g. with a separately deposited sealing layer. A planarization layer 13 is subsequently deposited over the whole surface, made of a material that can be e.g. thermally flowed (smoothed). As a material for this planarization layer 13, borophosphorsilicate glass (BPSG) can for example be used, with which a sufficiently flat surface is achieved. This planarization layer 13 can at the same time serve as a sealing layer for sealing the etching openings in the membrane, so that a separate sealing layer can be omitted. In these method steps, the ISFET is protected by the protective layer 8 in the region provided for the electrochemical sensor CS.

Due to the required fine structures of the additional integrated components (e.g. MOSFETs of the control circuit), a etching of contact holes in the planarization layer 13 ensues by means of dry etching. These contact holes, which create the vertical electrically conductive connections 12 to the parts of the components that are to be contacted, are filled with metal; a first metallization layer is then deposited and structured, so that contact surfaces and printed conductors 31 result. The contacts for the source S and drain D of the ISFET are likewise manufactured as contact hole fillings, in a region (in front of or behind the planes of the drawings in the figures) which in the subsequent part of the manufacturing process remains covered by the dielectric layers to be deposited. If necessary, for this purpose the nitride layer 7 is removed in places over the source and drain regions. The sensor layer 110, which in this exemplary embodiment is manufactured so as to be at least partly electrically conductive, and the doped region 5 are likewise provided with an electrical terminal during the manufacture of the contact hole fillings. The insulating regions 2 on the upper side of the substrate 1 serve as electrical insulation between this doped region 5 and the sensor layer 10, so that this doped region 5 and the membrane can be used as electrodes for a capacitive pressure measurement, as in the sensor described in German OS 44 41 908.

If necessary, additional surface-wide dielectric layers 14 can be deposited as insulation between different printed conductor planes (intermediate oxide, IMOX). Additional metallizations are deposited and are structured to form additional contact surfaces or printed conductors 32 and 33. Additional method steps for manufacturing the electrochemical sensor preferably follow the planar-oriented process steps (concerning entire layer planes, and producing no structurings that have several layer planes). The execution of the process is thus preferably next continued up to the complete manufacture of the various metallization planes. A protective layer 15 of plasma oxide, without nitride, is preferably deposited on the upper side.

Figure 2:
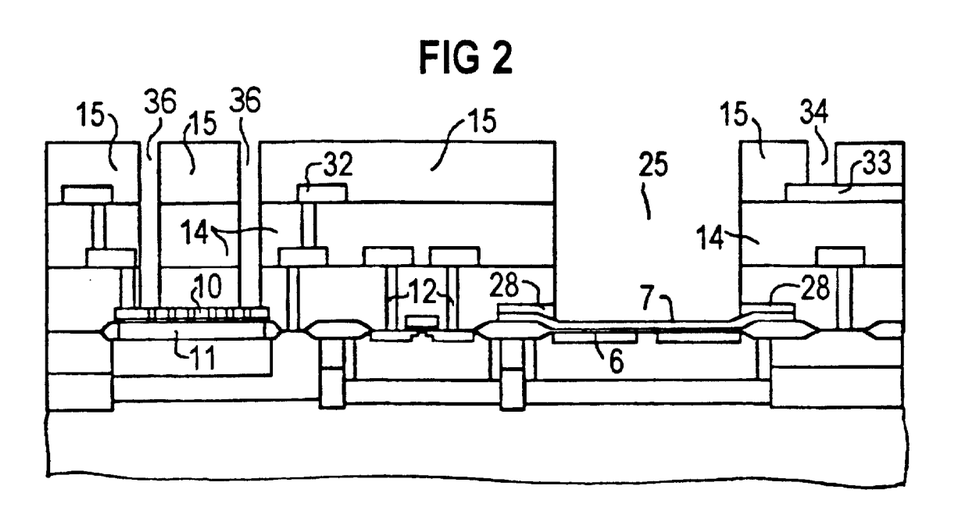
Figure 3:
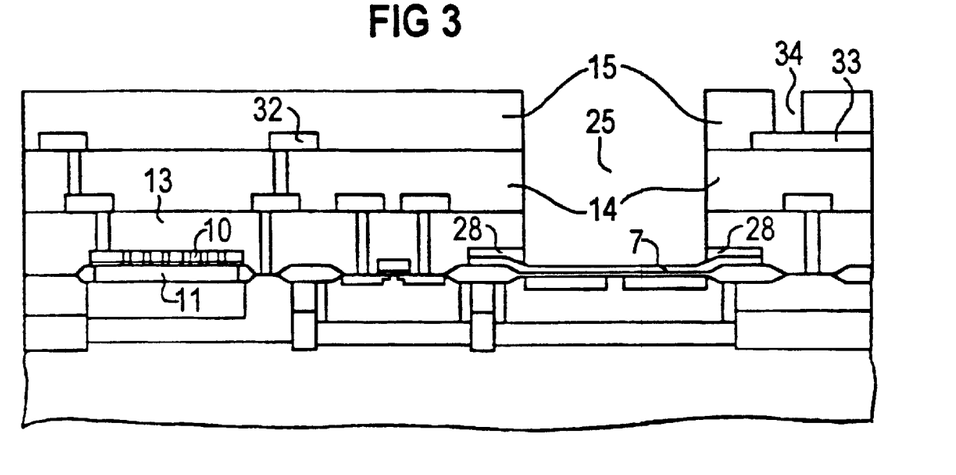
FIG. 3 shows the structure of FIG. 2 in a variant of the method.

In a first, preferred embodiment of the method, the etching free of the membrane of the pressure sensor and the opening of pads (connection points, small exposed terminal regions on the upper metallization plane 32) ensue in this upper protective layer 15 (see FIG. 2). A dry etching process is particularly suited for this purpose; however, wet-chemical etching is also possible in principle. If a connection of the noble metal electrodes (to be manufactured next) of the electrochemical sensor to a pad (provided for this purpose) of the upper metallization plane, or to components of the integrated circuit, is provided via the printed conductors, then, also for this purpose, in the upper protective layer 15 a contact hole 34 is etched up to the conductor 33 of the upper metallization plane, drawn in under the protective layer. As shown in FIG. 2, the dielectric layer structure 13, 14 and 15 can be left standing over the membrane of the pressure sensor in the middle, so that a piston-like structure modifies the inertia and flexibility of the membrane. In the view of FIG. 2, the depicted opening 36 forms a closed strip (e.g. in the shape of a hollow square or with an annular shape), and is considerably broader in relation to the thickness of the layers than is shown in FIG. 2, which is not to scale. In another variant of the method, the pressure sensor first still remains covered by the dielectric, as shown in FIG. 3. A contact hole 34 for the connection of the platinum contact is then preferably wet-chemically etched together with the etching free of the electrochemical sensor.

The opening 25 over the region of the ISFET, shown in FIGS. 2 and 3, is preferably wet-chemically etched, so that as little wearing away as possible of the nitride of the pH-sensitive layer occurs. The remaining portions 28 of the oxide layer 8, used in this example as a protective layer essential to the invention, are left over. The remaining method steps for the manufacture of the electrochemical sensor follow. A thin layer of the noble metal provided for the electrochemical sensor, e.g. platinum, is deposited on the upper protective layer 15, and is structured (e.g. using lift-off technique) to form a contact, designated simply as platinum contact 21 below (see FIGS. 4 to 6). In the explanation below, this noble metal electrode and its supply line are, for simplicity, referred to as the platinum contact (the metal may, however, alternatively be silver). The contact hole 34 can be filled at the same time as the depositing of the platinum, or can be filled separately beforehand with another metal. The platinum contact is deposited and structured in so that it is connected with the conductive connection 35 (which results from the filling of the contact hole 34) to the conductor 33 of the uppermost (deposited under the upper protective layer 15) metallization plane. This conductive connection 35 can be omitted if the platinum contact is to be contacted to a laterally arranged larger-surface region (pad). In a further variant of the method, the platinum contact is manufactured already before the etching of the opening 25. It then covers only a part of the surface of the upper protective layer 15. If the opening is etched before the manufacture of the platinum contact, the platinum contact can be deposited and structured in so that a substantial portion of the electrode formed by the platinium contact is deposited on the nitride layer laterally to the gate region. This is depicted schematically in the figures in such a way that the platinum contact covers a part of the drain region. In order to avoid possible parasitic capacitances, it can be advantageous to deposit the platinum contact laterally to the source, channel and drain, e.g. behind the plane of the drawing of the figures, behind the depicted channel region C.

Figure 4:
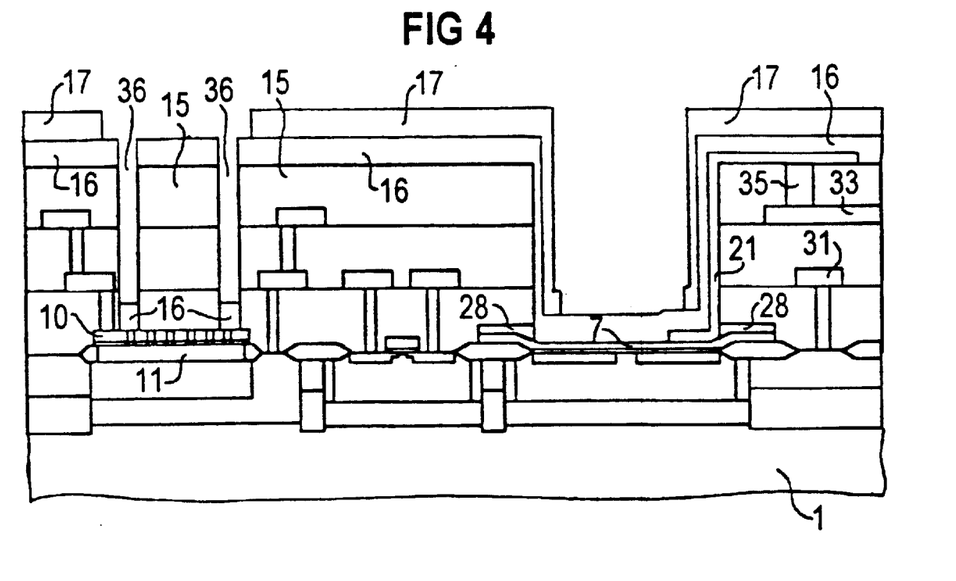
FIGS. 4 and 5 respectively show the structures of intermediate stages after the depositing of the noble metal electrode and the depositing of a two-layer protective layer for various exemplary embodiments.

An $SiO_2$ layer 16 and an $Si_3N_4$ layer 17, which are provided in particular as protective layers for the platinum contact, are deposited over the whole surface on the upper side, e.g. by means of PECVD (plasma enhanced chemical vapor deposition). This nitride layer 17 is then structured, and serves as a mask for further method steps. The removal of the oxide layer 16 up to the respectively desired portions belongs thereby occurs. FIG. 4 shows an exemplary embodiment in which an opening 36 of the pressure sensor is already etched and in which the platinum contact 21 has been deposited down to the base of the opening 25 of the electrochemical sensor. The oxide layer 16 is deposited with a thickness of e.g. 500 mm, and the nitride layer 17 is deposited with a thickness of e.g. 800 nm. The nitride layer 17 is structured so that it has openings in the regions of the terminal pads for external electrical connection, the portion of the electrochemical sensor to be exposed, and the pressure sensor again to be freed from the PECVD oxide. The PECVD oxide also covers the edges of the dielectric layers 13, 14 and 15 in the opening 36, and provides edge protection there as well. Due to lack of space, these parts of the oxide layer 16 are not depicted in the figures.

Figure 5:
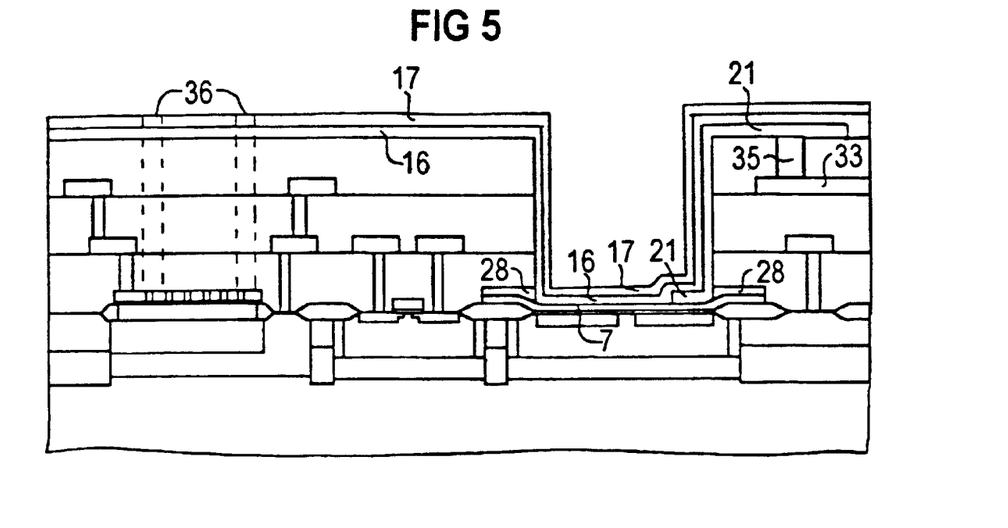

In contrast to FIG. 4, FIG. 5 shows a variant in which the pressure sensor is not etched free until later. After the etching of the opening 25 for the electrochemical sensor and the deposition of the platinum contact 21, the oxide layer 16 and the nitride layer 17 are deposited using PECVD. The nitride layer 17 is structured. Using a paint mask deposited for this purpose, or using the structured nitride layer 17 as a mask, the opening 36 (shaped e.g. as a hollow cylinder) is etched above the pressure sensor membrane indicated in dotted lines in FIG. 6. This preferably takes place with a dry etching method. Afterwards, the nitride layer 17 is etched in the region of the terminal pads for external electrical connection and in the region of the portion to be exposed in the electrochemical sensor, which preferably takes place by means of a wet-chemical method. During this etching, the pressure sensor is protected by a covering paint mask. As a protective layer over the platinum contact, a unilayer can be provided, e.g., an oxide layer such as $SiO_2$ or TEOS. The specified method with a separate oxide layer 16 and nitride layer 17, however, has the advantage that the nitride layer can be used as a mask for subsequent method steps.

After the membrane of the pressure sensor has been freed, to the extent provided, from the dielectric material present thereon, and the nitride layer 17 has been completely structured, a first polymer layer 18 and a second polymer layer 19 are deposited (in both cases preferably polyimide or polybenzoxazole) and are structured suitably for the manufacturing of micro-pools. All the oxides are subsequently wet-chemically etched, whereby the nitride layer 17 (and, if warranted, the first polymer layer 18, if the structure of FIG. 7 described below, is manufactured) is used as a mask. Given a suitable structuring of the nitride layer 17, the removal of the PECVD oxide layer 16 in the region of the pressure sensor can be carried out in so that a piston, made of the remainder of the dielectric layer, is left standing in the middle of the membrane, with a predetermined thickness. In a preferred embodiment, the etching openings in the sensor layer 10 are made only at those points at which this piston remains standing, so that during the removal of the portions of the oxide layer 16 deposited on the membrane, all etching openings remain protected by the thick piston, which is worn away only slightly. (The outermost etching openings of those shown (only schematically) in FIGS. 4 to 6 would thus be omitted.)

Figure 6:
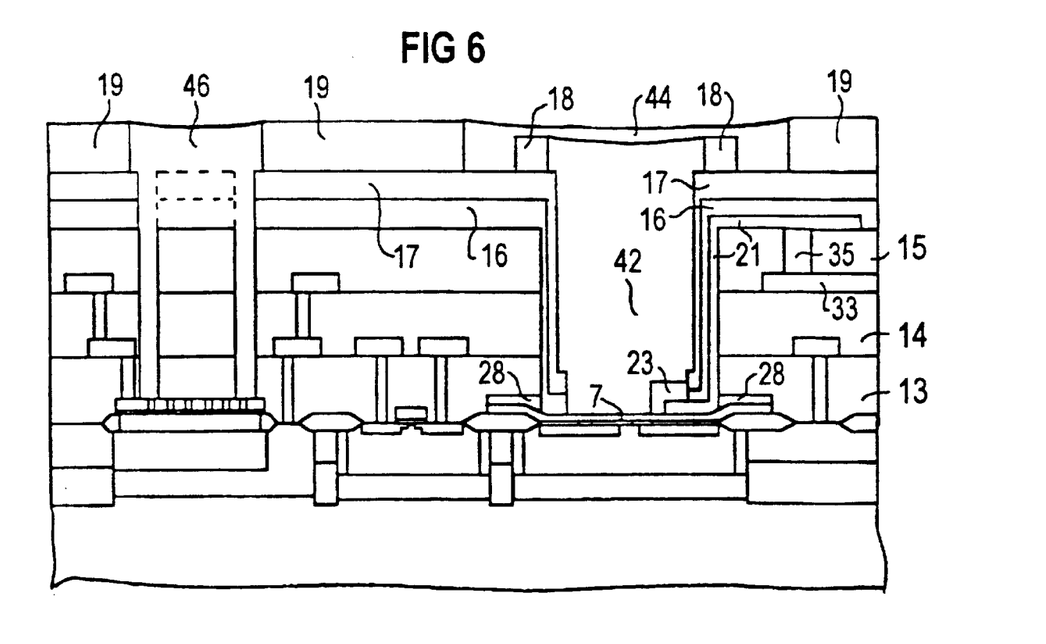
FIGS. 6 and 7 show the result of the inventive method for the example of a potentiometric sensor for various exemplary embodiments.

The wet-chemical etching (without photo technique) of the oxide in the region of the electrochemical sensor takes place in a protective fashion, i.e. with a low etching rate at least in the last etching phase, in order to minimize any wearing away of the nitride of the nitride layer 7, deposited by means of LPCVD. This nitride layer 7 or the platinum contact 21 then serves as an etching stop layer. Silver is deposited (e.g. galvanically) on an exposed part of the platinum contact 21. This later silvering of the platinum contact can be omitted if silver was used instead of platinum as a material for the noble metal electrodes. This silver is partly converted to silver chloride, chemically or electrochemically (e.g. in a chloride bath). The pads for external connection are protected with paint masks during this method step. In manufacturing a conductometric sensor that measures only the conductivity between different electrodes, the Ag/AgCl contact can be omitted. An electrolyte layer 42, bordered by the structure of the first polymer layer 18, is then deposited in the opening 25, and a hydrophobic layer 44, bordered by the structure of the second polymer layer 19, is deposited thereon and laterally thereto. In this way, the structure shown in FIG. 6 is obtained. In the embodiment shown in FIG. 6, a further layer 46, made e.g., of the material of the hydrophobic layer 44, is built into the opening above the pressure sensor membrane as a protective layer for the pressure sensor. According to variants of the method (etching free of the pressure sensor after depositing the PECVD oxide layer 16 and the PECVD nitride layer 17, or a renewed wearing away of oxide from the previously already-exposed pressure sensor region), the layer portion shown with a dotted line in FIG. 6 can be optionally present above the pressure sensor.

Figure 7:
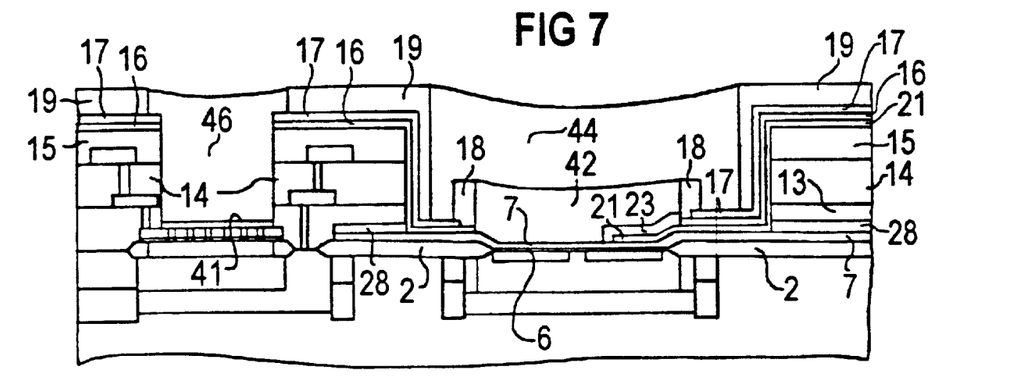

FIG. 7 shows an alternative embodiment in which the first polymer layer 18 is deposited and structured inside the opening etched for the electrochemical sensor. The edges of the nitride layer 17 in the interior of the opening provided for the sensor are located under the structured first polymer layer 18, provided as a border for the electrolyte layer 42. This polymer layer 18 also serves as a mask for the removal of the oxide layer 16 in the region of the electrochemical sensor, so that, as shown, the inner edges of the oxide layer 16 terminate conformally with the inner edges of the structured polymer layer 18. The platinum contact 21 is deposited in the interior of the region bordered by the first polymer layer 18, and is provided with an outward supply line. This supply line is protected toward the hydrophobic layer 44 by the double layer of the oxide layer 16 and the nitride layer 17. The supply line of the platinum contact 21 is laterally constructed on the layer sequence of the dielectrics 13, 14 and 15. Underneath the electrolyte layer 42, the platinum contact 21 is completely covered with the Ag/AgCl contact 23. The structuring of the second polymer layer 19 ensues, as shown, such that the second polymer layer 19 is removed at least above the opening provided for the pressure sensor, and such that the second polymer layer 19 is removed at least above the opening provided for the pressure sensor, and such that the second polymer layer 19 leaves open a sufficient portion outside the border formed by the first polymer layer 18 in the interior of the opening provided for the electrochemical sensor. As shown, the second polymer layer 19 will cover, in surrounding fashion, the edges of the bordering layers in the interior of the opening provided for the electrochemical sensor, i.e., here in particular the surfaces of the nitride layer 17 that are present at that location.

For clarity, FIG. 7 also indicates additional specified variants of the inventive method. The remaining portions 28 of the lower protective layer are not shown in FIG. 7 as being limited to the region of the electrochemical sensor CS, but leave the region of the pressure sensor free. The membrane of the pressure sensor is here etched free, as an example, in the entire surface provided for a measurement. The depicted sealing layer 41 can be a lowest layer portion of the planarization layer 13, which is not removed during the etching, or can be a separately deposited layer, which can for example be made of metal and for example can serve for the adding rigidity to the membrane, or as a counter-electrode.

Figure 8:
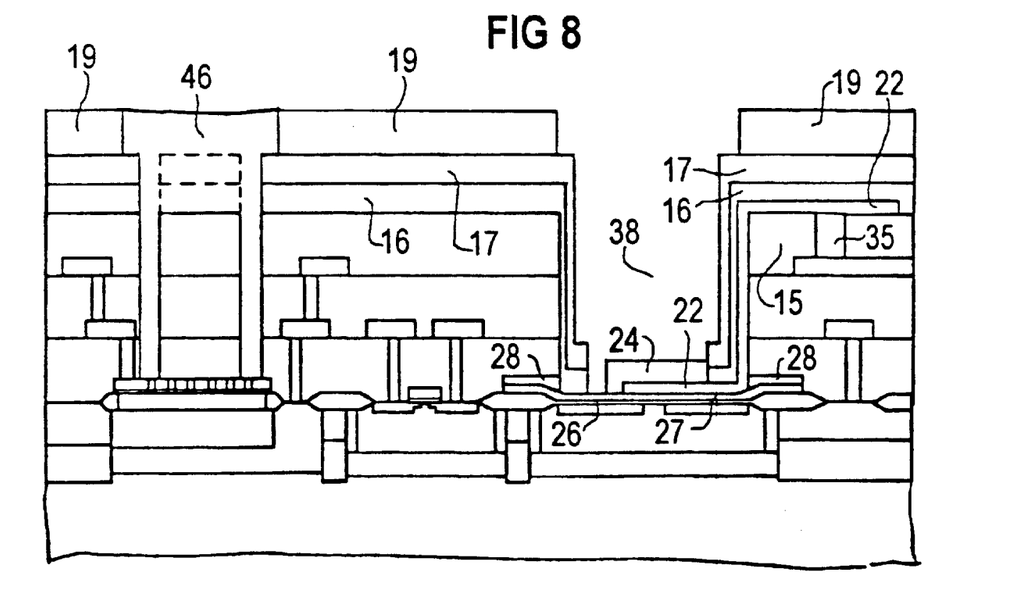
FIGS. 8 and 9 show the result of the inventive method for examples with a potentiometric reference sensor.

In addition to the electrochemical sensor, a further structure can be manufactured that has the same basic structure as the sensor, but behaves neutrally in relation to the chemical material whose concentration is to be determined. In an embodiment with a potentiometric sensor with an ISFET, a reference ISFET, provided for a comparison measurement (difference measurement) can be manufactured. For the reference ISFET, a basic structure of the same type as for the sensor provided for the direct measurement is manufactured. According to the representation in FIG. 8, this basic structure has an oxide layer 26 on the channel region and a pH-sensitive layer, e.g. a nitride layer 27. By means of an etching process, before the manufacturing of the platinum contact, the dielectric layers 13, 14 and 15 are removed in the region of the reference ISFET down to the nitride layer 27, so that the opening 38 arises and the nitride layer is at least partially exposed. This etching is preferably carried out together with the wet-chemical etching step for the manufacture of the opening 25 above the actual sensor. At the same time contact holes (contact hole 34 for the connection of the platinum contact to the uppermost metallization plane; cf. FIG. 2 or 3) can also be etched into the upper protective layer 15. The leftover lateral remainder 28 of the lower protective layer 8 is shown in FIG. 8. Together with the manufacture of the platinum contact 21 for the actual sensor, an additional platinum contact 22 is deposited in the region of the reference ISFET, and is structured on the pH-sensitive layer (nitride layer 27), on the edges of the opening 38 and on a part of the bordering upper side of the protective layer 15. This deposition takes place in such a way that this additional platinum contact 22 covers the channel region of the ISFET and is provided with an electrical connection to the circuit parts provided for the comparison measurement, e.g., as shown, via a contact hole filling 45 with a conductor 43 of the uppermost metallization plane of the electronic circuit. Subsequently, as specified above, the $SiO_2$ layer 16 and the $Si_3N_4$ layer 17 are deposited and structured using PECVD, and the second polymer layer 19 is deposited and structured. All the oxide is also wet-chemically etched in the region of the reference ISFET, with the nitride layer 17, or a paint mask again being used for structuring the nitride layer 17, functioning as a mask. A layer of silver is deposited (e.g. galvanically) on the platinum metallization 22, which is partly converted into silver chloride chemically or electrochemically (e.g. in a chloride bath), so that the Ag/AgCl contact 24 is formed. It is not necessary to deposit an electrolyte layer or a hydrophobic layer on the reference ISFET. The execution and sequence of the remaining method steps correspond to those described above for the electrochemical sensor.

Figure 9:
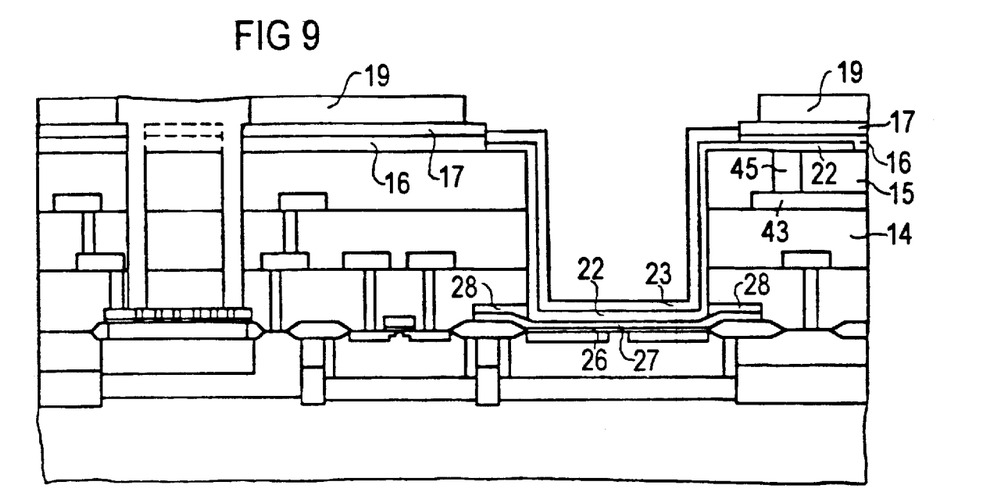

FIG. 9 shows an alternative embodiment for the structure formed with the reference ISFET, in combination with constructions of the entire arrangement, as shown in FIG. 6. The additional platinum contact 22 is deposited over the entire surface on the nitride layer 27 and on the edges of the dielectric layers 13, 14 and 15, and is covered over its whole surface with the Ag/AgCl contact 23. This construction is independent of the specific constructions of the remaining components of the arrangement, so that these whole-surface contacts can also be provided in the variants of the pressure sensor of FIG. 7.

A MOSFET with the same lateral dimensions and the same layer structure (oxide layer and nitride layer in the gate region) as the ISFET provided for the potentiometric sensor is manufactured with the same method steps provided for the reference ISFET. The deposition of the Ag/AgCl contact is thus omitted, and the opening above this MOSFET is sealed with the PECVD oxide layer and the PECVD nitride layer, and, if necessary, also with the second polymer layer 19. This MOSFET is used as a reference component in order to have a reference quantity during the measurement, and is a component of the evaluation circuit.

Figure 10:
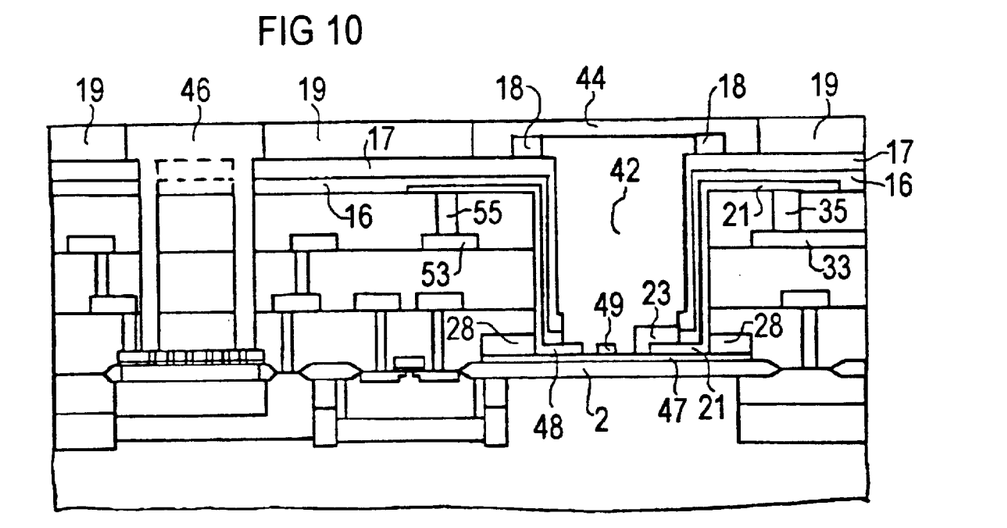
FIG. 10 shows the result of the inventive method for the example of an amperometric sensor.

The inventive method is not limited to the manufacture of potentiometric electrochemical sensors with ISFET; FIG. 10 shows a structure corresponding to the representation in FIG. 6 for the example of an amperometric sensor. Corresponding to the specification in European Application 0 465 708 (cited above), the amperometric sensor has at least one noble metal electrode as a counter-electrode to a working electrode made of noble metal or of carbon, and, if necessary, an additional noble metal electrode as a reference electrode. In the example of FIG. 10, a platinum contact 21 can be provided with the Ag/AgCl contact 23, deposited thereon, or a silver contact can be provided as a reference electrode. An additional platinum contact 48 is preferably connected in an electrically conductive fashion via a contact hole filling 55 with a printed conductor 53 of the upper metallization plane of the CMOS wiring, and serves as a working electrode. The counter-electrode is formed by a third platinum contact 49 that is deposited between the working electrode 48 and the reference electrode 21/23, and is electrically connected in an analogous way in front of or behind the plane of the drawing. The basic structure of an ISFET is omitted here, however, a nitride layer 47 is preferably also present in the amperometric sensor as a base for the electrode arrangement. As insulation against the substrate 1, a flat insulating region 2 is preferably present in the region of the amperometric sensor. This insulating region 2 is made insulating by means of thermal oxidation (LOCOS). The nitride layer 47 can be deposited in planar fashion on this insulating region 2. This depositing also takes place preferably, but not necessarily, by means of LPCVD. For the amperometric sensor, an electrolyte layer 42 and a hydrophobic layer 44 can likewise be provided, or the noble metal electrodes are covered with a hydrophilic membrane, as described in European Application 0 465 708.

In the case of a conductometric sensor, two electrodes are manufactured that are arranged immediately adjacent to one another, with their largest possible surfaces facing one another, e.g. interlocked in comb fashion, in order to be able to determine the change in conductivity of a surrounding medium. A covering of the electrodes can be carried out for protection, as in the case of the pressure sensor, or can be omitted. As described for the example of the amperometric sensor, the manufacture of the electrodes and of the electrical terminal ensues substantially in the same method sequence.

The inventive method is preferably carried out in the context of a CMOS process or bi-CMOS process, or in a manner analogous to a CMOS process or bi-CMOS process. The additional components that are to be monolithically integrated together with the sensors, and that form the electronic circuit for control and evaluation, can be manufactured in the context of this process, e.g. as MOSFETs.

In the figures, as an example a MOSFET is depicted as a component of an electronic circuit EC that is manufactured in the doped region 4 and is electrically insulated from the remaining components by means of the oxidized regions 2. Thus, with the method disclosed herein, a very extensive integration of electronic components to form the sensors is possible.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for manufacturing a combination of a pressure sensor and an electrochemical sensor by integrating a micromechanical pressure sensor and an electrochemical sensor on a substrate, comprising the steps of:
   (a) forming a plurality of electrically conductive regions in a substrate;
   (b) forming a basic structure for an electrochemical sensor on said substrate, said basic structure comprising at least one electrically insulating layer;
   (c) covering said basic structure of said electrochemical sensor with a protective layer and leaving a first free region for a pressure sensor;
   (d) depositing a sensor layer for said pressure sensor in said first free region and providing said sensor layer with etching openings;
   (e) etching out a hollow space between said sensor layer and said substrate, steps (a) through (e) producing an intermediate structure having an outermost surface;
   (f) depositing a planarization layer of a dielectric material over an entirety of said outermost surface of said intermediate structure;

(g) providing regions for electrical connection to said intermediate structure and producing electrically conductive connections to said regions for electrical connection;

(h) outwardly exposing said sensor layer of said pressure sensor;

(i) etching a second free region for said electrochemical sensor and depositing and structuring at least one noble metal electrode in said second free region;

(j) depositing an additional protective, layer over said noble metal electrode; and (k) depositing and structuring a plurality of additional layers for said electrochemical sensor.

2. A method as claimed in claim 1 wherein step (h) comprises outwardly exposing said sensor layer of said pressure sensor by dry etching.

3. A method as claimed in claim 1 wherein step (b) comprises depositing a nitride layer as said at least one insulating layer and wherein step (i) comprises etching said second free region for said electrochemical sensor including removing said protective layer by wet-chemical etching.

4. A method as claimed in claim 1 wherein step (j) comprises depositing an oxide layer by PECVD, followed by depositing a nitride layer.

5. A method as claimed in claim 1 wherein step (i) comprises first etching said second free region for said electrochemical sensor including removing said protective layer in said region, and depositing a platinum metallization as said noble metal electrode and structuring said platinum metallization to form a platinum contact covering at least a portion of said insulating layer of said basic structure of said electrochemical sensor and a portion of edges of layers lateral to the second free region.

6. A method as claimed in claim 1 wherein step (b) comprises manufacturing a basic structure for said electrochemical sensor comprising an ISFET, and wherein step (i) further comprises providing said noble metal electrode with a silver contact.

7. A method as claimed in claim 1 wherein step (b) comprises manufacturing a basic structure for said electrochemical sensor comprising an ISFET, and wherein step (i) further comprises providing said noble metal electrode with a silver chloride contact.

8. A method as claimed in claim 1 wherein step (c) comprises producing said protective layer by depositing an oxide layer and partially removing said oxide layer.

9. A method as claimed in claim 1 comprising the additional step of integrating said pressure sensor and said electrochemical sensor with an electronic circuit including, in step (a) providing at least one component of said electronic circuit on said substrate and conducting steps (a), (f) and (g) as steps in a CMOS process for integrating said electronic circuit.

10. A method as claimed in claim 9 wherein step (g) comprises manufacturing contact holes in said planarization layer, said contact holes comprising said regions for electrical connection, by dry etching and filling said contact holes with electrically conductive material and depositing and structuring at least one metallization plane for printed conductors over said planarization layer.

11. A method as claimed in claim 1 wherein step (b) comprises manufacturing said basic structure as an ISFET and comprising the additional step of manufacturing an additional basic structure comprising a reference ISFET and wherein step (a) comprises forming electrically conductive regions in said substrate for said ISFET and for said reference ISFET, wherein step (c) includes covering said ISFET with said protective layer, and wherein step (i) comprises first etching said second free region for said electrochemical sensor and a third free region for said reference ISFET by removing said protective layer in both said second and third free regions, and depositing and structuring a further noble metal electrode in said third free region for said reference ISFET by depositing a platinum metallization in said third free region and structuring said platinum metallization to form a platinum contact covering at least a channel region of said reference ISFET and a portion of edges of layers arranged laterally to said third free region.

12. A method for manufacturing a combination of a pressure sensor and an electrochemical sensor by integrating a micromechanical pressure sensor and an electrochemical sensor on a substrate, comprising the steps of:

(a) forming a plurality of electrically conductive regions in a substrate;

(b) forming a basic structure for an electrochemical sensor on said substrate, said basic structure comprising at least one electrically insulating layer;

(c) covering said basic structure of said electrochemical sensor with a protective layer and leaving a first free region for a pressure sensor;

(d) depositing a sensor layer for said pressure sensor in said first free region and providing said sensor layer with etching openings;

(e) etching out a hollow space between said sensor layer and said substrate, steps (a) through (e) producing an intermediate structure having an outermost surface;

(f) depositing a planarization layer of a dielectric material over an entirety of said outermost surface of said intermediate structure;

(g) providing regions for electrical connection to said intermediate structure and producing electrically conductive connections to said regions for electrical connection;

(h) etching a second free region for said electrochemical sensor and depositing and structuring at least one noble metal electrode in said second free region;

(i) depositing an additional protective layer over said noble metal electrode;

(j) outwardly exposing said sensor layer of said pressure sensor; and (k) depositing and structuring a plurality of additional layers for said electrochemical sensor.

13. A method as claimed in claim 12 wherein step (j) comprises outwardly exposing said sensor layer of said pressure sensor by dry etching.

14. A method as claimed in claim 12 wherein step (b) comprises depositing a nitride layer as said at least one insulating layer and wherein step (h) comprises etching said second free region for said electrochemical sensor including removing said protective layer by wet-chemical etching.

15. A method as claimed in claim 12 wherein step (i) comprises depositing an oxide layer by PECVD, followed by depositing a nitride layer.

16. A method as claimed in claim 12 wherein step (h) comprises first etching said second free region for said electrochemical sensor including removing said protective layer in said region, and depositing a platinum metallization as said noble metal electrode and structuring said platinum metallization to form a platinum contact covering at least a portion of said insulating layer of said basic structure of said electrochemical sensor and a portion of edges of layers lateral to the second free region.

17. A method as claimed in claim 12 wherein step (b) comprises manufacturing a basic structure for said electrochemical sensor comprising an ISFET, and wherein step (h) further comprises providing said noble metal electrode with a silver contact.

18. A method as claimed in claim 12 wherein step (b) comprises manufacturing a basic structure for said electrochemical sensor comprising an ISFET, and wherein step (h) further comprises providing said noble metal electrode with a silver chloride contact.

19. A method as claimed in claim 12 wherein step (c) comprises producing said protective layer by depositing an oxide layer and partially removing said oxide layer.

20. A method as claimed in claim 12 comprising the additional step of integrating said pressure sensor and said electrochemical sensor with an electronic circuit including, in step (a) providing at least one component of said electronic circuit on said substrate and conducting steps (a), (f) and (g) as steps in a CMOS process for integrating said electronic circuit.

21. A method as claimed in claim 20 wherein step (g) comprises manufacturing contact holes in said planarization layer, said contact holes comprising said regions for electrical connection, by dry etching and filling said contact holes with electrically conductive material and depositing and structuring at least one metallization plane for printed conductors over said planarization layer.

22. A method as claimed in claim 12 wherein step (b) comprises manufacturing said basic structure as an ISFET and comprising the additional step of manufacturing an additional basic structure comprising a reference ISFET and wherein step (a) comprises forming electrically conductive regions in said substrate for said ISFET and for said reference ISFET, wherein step (c) includes covering said ISFET with said protective layer, and wherein step (h) comprises first etching said second free region for said electrochemical sensor and a third free region for said reference ISFET by removing said protective layer in both said second and third free regions, and depositing and structuring a further noble metal electrode in said third free region for said reference ISFET by depositing a platinum metallization in said third free region and structuring said platinum metallization to form a platinum contact covering at least a channel region of said reference ISFET and a portion of edges of layers arranged laterally to said third free region.

* * * * *